March 31, 1953 H. C. SWIM Plant Pat. 1,176
ROSE PLANT
Filed March 27, 1952
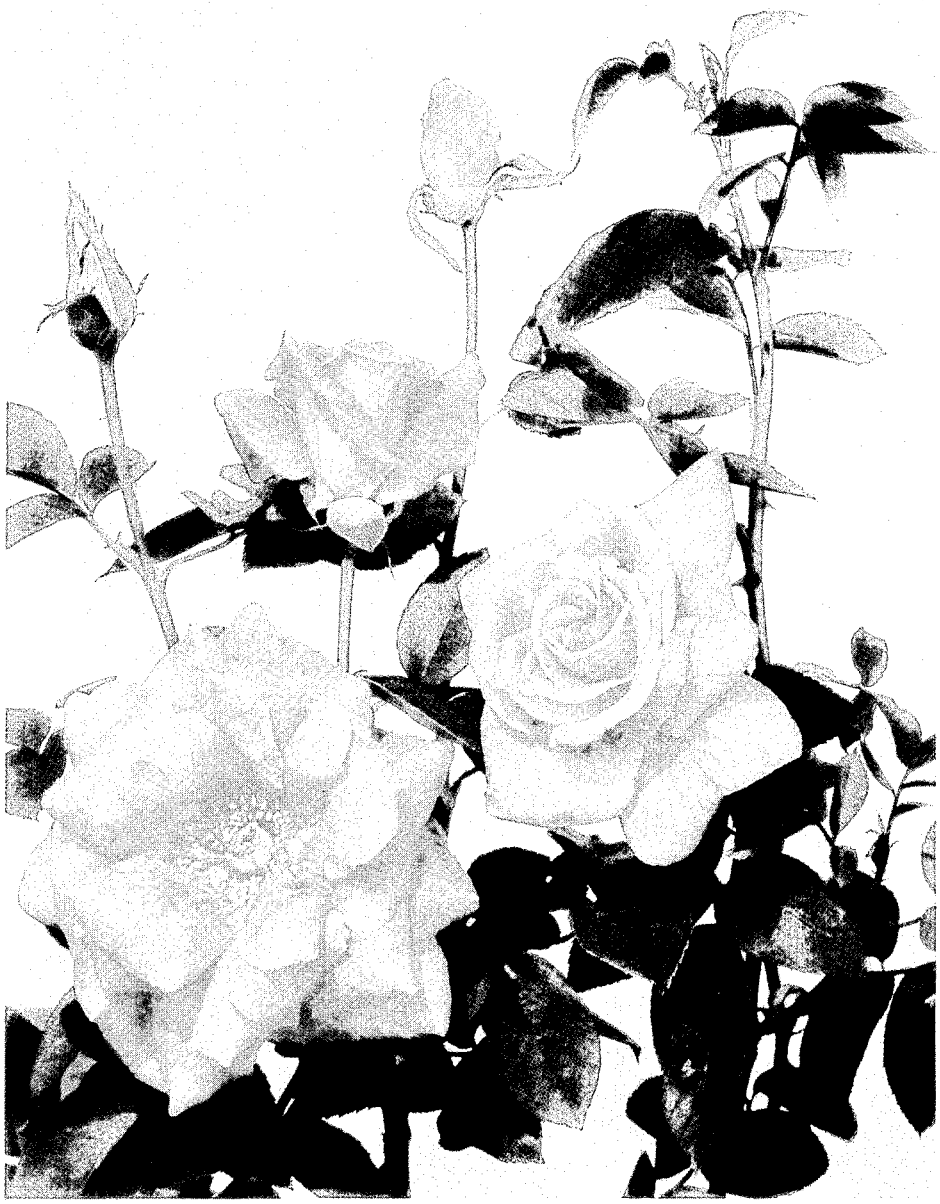
Inventor.
H. C. Swim
By: Robert Cobb
Attorneys.

Patented Mar. 31, 1953

Plant Pat. 1,176

UNITED STATES PATENT OFFICE 1,176

ROSE PLANT

Herbert C. Swim, Ontario, Calif., assignor to Armstrong Nurseries, Inc., Ontario, Calif., a corporation of California Application March 27, 1952, Serial No. 278,774

1 Claim. (Cl. 47—61)

The present invention relates to a new and distinct variety of rose plant of the hybrid tea class, originated by me by crossing the variety "Charlotte Armstrong" (Plant Patent No. 455) with the variety "Signora Piero Puricelli," known in the United States as "Signora" (Plant Patent No. 201).

My new variety is distinct from every other rose of its class by reason of its new combination of outstanding characteristics as follows:

(1) Few to no prickles on its long flowering stems;

(2) Blooms usually borne singly;

(3) Better than average lasting quality of the blooms;

(4) Semi-double form of the blooms which are high-centered as they first open, but become saucer-shaped with maturity;

(5) Petals of orange-red general tonalty, and wider and longer than average and having better than average substance, with prominent veins showing throughout the life of the blooms.

In comparison with its seed parent "Charlotte Armstrong," the new variety substantially differs from the same, as evidenced by the fact that the plants exhibit a more upright habit of growth; there are fewer prickles on the flowering stems, as well as on the plants as a whole; the blooms are popularly described as orange-red in color, whereas those of "Charlotte Armstrong" are ordinarily described as blood-red to cerise; the blooms are semi-double in form, while those of the seed parent are classified as double; and the foliage is quite glossy, while that of "Charlotte Armstrong" is considered non-glossy.

Compared with its pollen parent "Signora," my new variety has a substantially longer bud form and the buds are long pointed to long urn-shaped; the peduncle has soft prickles, while the pollen parent has numerous stiff and heavy prickles on the peduncle; the petals of the semi-double blooms are of heavier substance and are more uniform in size, generally longer and wider, and there are fewer petaloids (3 to 5), as compared with the petals of the double blooms of "Signora"; the color of the mature foliage is a lighter shade of green than that found on the pollen parent, while the reddish-purple and green colors of the young growth are also lighter in shade than in this parent.

Asexual reproduction of the new variety by budding at Ontario, California, shows that the foregoing characteristics and distinctions come true to form and are established and transmitted through succeeding propagations.

The accompanying drawing shows specimens of my new variety, with the flowers and foliage in different stages of development.

The following is a detailed description of the new variety, with color terminology in accordance with Robert F. Wilson's Horticultural Colour Chart, except where color terms from Ridgway's Color Standards and Nomenclature are indicated, or where color terms of ordinary dictionary significance are obvious:

Type: Outdoor; seedling; for cut flowers and for garden decoration.

Class: Hybrid Tea.

Breeding: Seedling.

*Seed parent.*—"Charlotte Armstrong."

*Pollen parent.*—"Signora."

Propagation: Holds its distinguishing characteristics through succeeding propagations by budding.

*Flower*

Locality where grown and observed: Ontario, California.

Flowers borne: Usually singly to stem; on strong, long stems.

Quantity of bloom: Free; outdoors.

Continuity: Nearly continuous during growing season.

Fragrance: Moderate; tea.

Bud:

*Peduncle.*—Average length; average caliper to heavy; erect; smooth; numerous gland-tipped cilia; and very few weak prickles. Color—between Kildare Green, Plate XXXI (Ridgway) and Absinthe Green, Plate XXXI (Ridgway).

*Before calyx breaks.*—Size—medium to large. Form—long pointed; with foliaceous appendages on alternate sepals; some gland-tipped cilia; usually with bristle-like foliaceous parts extending beyond the tip of the bud equal to one-fourth to one-half of its length.

*As calyx breaks.*—Color—between Mandarin Red, Plate 17/1, page 17, and Vermilion, Plate 18/1, page 18, with shadings of Cadmium Orange, Plate 8/1, page 8, to Tangerine Orange, Plate 9/1, page 9.

*Sepals.*—Inner surface—with fine, woolly tomentum; margins with alternate sepals having woolly tomentum; others with foliaceous appendages and stipitate glands and hairs.

*As first petal opens.*—Size—large. Form—long; pointed to long urn-shaped. Color—outside: between Mandarin Red, Plate 17/2, page 17, and Vermilion, Plate 18/2, page 18, with shadings of Cadmium Orange, Plate 8/2, page 8, and Tangerine Orange, Plate 9/2, page 9; small area at base near attachment Lemon Yellow, Plate 4/1, page 4; inside: between Poppy Red, Plate 16/1, page 16, and Mandarin Red, Plate 17/1, page 17, shaded with near Vermilion, Plate 18/2, page 18; small area at base near attachment Lemon Yellow, Plate 4/1, page 4.

*Opening.*—Opens up well; is not retarded from opening by cold, hot, wet or dry weather.

Bloom:

*Size, when fully open.*—Large; 4 inches to 4½ inches.

*Petalage.*—Semi-double; from 20 to 26 petals, plus 3 to 5 petaloids; arranged regularly.

*Form.*—High-centered at first; becoming open to saucer shape; petals being at first cupped, with tips rolled outward; becoming later, at maturity, loosely cupped, with tips rolled outward.

Petals:

*Texture.*—Medium to thick; moderately leathery; with inside satiny and outside slightly shiny to satiny.

*Shape.*—Outside—obovate, with apex flat; sometimes with 1 to 2 notches. Intermediate—obovate, with apex rounded to flat; sometimes with 1 to 2 notches. Inside—obovate; somewhat irregular, with apex rounded; sometimes with 1 to 2 notches.

This description of a newly opened flower was made from a rose grown outdoors in the month of August, at Ontario, California:

*Color.*—Outside petal—outside surface: near Mandarin Red, Plate 17/2, page 2, with shading of near Scarlet, Plate 19/2, page 19, near margin: prominent veins near Saturn Red, Plate 13, page 13; small area at base Lemon Yellow, Plate 4/1, page 4; inside surface: near Mandarin Red, Plate 17/1, page 17, and Vermilion, Plate 18/1, page 18; veins near Saturn Red, Plate 13/2, page 2; small area at base near attachment, near Lemon Yellow, Plate 4/1, page 4. Intermediate petal—outside surface: near Mandarin Red, Plate 17/2, page 17, with shadings of near Scarlet, Plate 19/2, page 19, near margin; prominent veins near Saturn Red, Plate 13, page 13; small area at base near Lemon Yellow, Plate 4/1, page 4. Inside surface: near Mandarin Red, Plate 17/1, page 17, and Vermilion, Plate 18/1, page 18; veins near Saturn Red, Plate 13/2, page 13; small area at base near attachment near Lemon Yellow, Plate 4/1, page 4. Inner petal—outside surface: near Mandarin Red, Plate 17/2, page 17, with shadings of near Scarlet, Plate 19/2, page 19, near margin; prominent veins near Saturn Red, Plate 13, page 13; small area at base near Lemon Yellow, Plate 4/1, page 4; inside surface—near Mandarin Red, Plate 17/1, page 17, and Vermilion, Plate 18/1, page 18; veins near Saturn Red, Plate 13/2, page 13; small area at base near attachment, near Lemon Yellow, Plate 4/1, page 4.

This description was made from a rose that was open for three days outdoors in the month of September, at Ontario, California:

*Color.*—Outside petal—outside surface: near Scarlet, Plate 19/3, page 19, with shadings of Cadmium Orange, Plate 8/3, page 8; small area at base near attachment near Lemon Yellow, Plate 4/1, page 4; inside surface: near Scarlet, Plate 19/3, page 19, with prominent veins near Fire Red, Plate 15/2, page 15; small area at base near attachment near Lemon Yellow, Plate 4/1, page 4. Inside petal—outside surface: near Scarlet, Plate 19/3, page 19, and Mandarin Red, Plate 17/3, page 17, with shadings of Cadmium Orange, Plate 8/3, page 8; small area at base near attachment Lemon Yellow, Plate 4/1, page 4; inside surface: near Scarlet, Plate 19/2, page 19, and Mandarin Red, Plate 17/2, page 17; small area at base near attachment Lemon Yellow, Plate 4/1, page 4.

*General color effect.*—Newly opened flower—near Saturn Red, Plate 13/1, page 13, and Nasturtium Red, Plate 14/1, page 14, with shadings of near Scarlet, Plate 19/2, page 19, and with prominent veins standing out on outer petal near Poppy Red, Plate 16/2, page 16. Three days open—near Scarlet, Plate 19/3, page 19, with some Mandarin Red, Plate 17/3, page 17; small area at base Lemon Yellow, Plate 4/1, page 4.

*Behavior.*—Drop off cleanly; not particularly affected by cold, hot, wet or dry weather, except that the color of the blooms fade somewhat in very hot weather.

*Flower longevity.*—On bush in garden—3 to 4 days in September. Cut roses grown outdoors kept at living-room temperatures—3 days in September.

*Reproductive organs*

Stamens: Average number; arranged regularly about pistils.

Filaments: Medium length; 8 to 12 mm. long; most with anthers. Color—near Mandarin Red, Plate 17/1, page 17.

Anthers: Medium size to large; all open at once approximately. Color—upper side: margin near Scarlet, Plate 19/1, page 19; remainder near Indian Yellow, Plate 6/2, page 6; under side: margin near Saffron Yellow, Plate 7/2, page 7; remainder near Aureolin, Plate 3/3, page 3.

Pollen: Moderate to abundant. Color—between Indian Yellow, Plate 6/1, page 6, and Saffron Yellow, Plate 7, page 7.

Pistils: Many; approximately 85 in number.

Styles: Moderately even; average length; average caliper; bunched. Color—near Scarlet, Plate 18, page 18, changing to near Lemon Yellow, Plate 4/2, page 4, toward ovary.

Stigma: Color—near Aureolin, Plate 3/3, page 3.

Ovaries: Most protruding from calyx.

Sepals: Permanent; recurved. Color—inside: between Calliste Green, Plate VI (Ridgway) and Parrot Green, Plate VI (Ridgway), masked with white tomentum; outside: between Calliste Green, Plate VI (Ridgway) and Parrot Green, Plate VI (Ridgway).

Seeds: Rarely sets seeds.

*Plant*

Foliage:

*Leaves.*—Compound of usually 3 to 5 leaflets; normal abundance; large; somewhat leathery and semi-glossy.

*Leaflets.*—Shape—ovoid, with apex acute; base—round; margin—simply serrate.

*Color.*—Mature—upper surface: between Bice Green, Plate XVII (Ridgway) and Forest Green, Plate XVII (Ridgway); under surface: between Courge Green, Plate XVII (Ridgway) and Biscay Green, Plate XVII (Ridgway). Young—upper surface: near Calla Green, Plate V (Ridgway); shaded particularly around margins with near Dark Mineral Red, Plate XXVII (Ridgway); under surface: near Kildare Green, Plate XXXI (Ridgway), shaded with near Mineral Red, Plate XXVII (Ridgway) and Hydrangea Red, Plate XXVII (Ridgway).

*Rachis.*—Average size. Upper side—grooved; some stipitate glands on edges. Under side—smooth, with stipitate glands. Only an occasional prickle on under side.

*Stipules.*—Medium length; medium width; moderately short points turning out at an angle of less than 45°.

*Disease.*—Average resistance to mildew as determined by comparison with other varieties grown under comparable conditions.

Growth:

*Habit.*—Upright; much branched.

*Growth.*—Very vigorous.

*Canes.*—Heavy.

*Main stems.*—Color—between Yellowish Oil Green, Plate V (Ridgway) and Oil Green, Plate V (Ridgway). Large prickles—several; medium length; hooked slightly downward; with medium-length, moderately narrow base. Color—between Pecan Brown, Plate XXVIII (Ridgway) and Rood's Brown, Plate XXVIII (Ridgway). Small prickles—none. Hairs—none.

*Branches.*—Color—between Lettuce Green, Plate V (Ridgway) and Parrot Green, Plate VI (Ridgway). Large prickles—few to several; medium length; hooked slightly downward; with medium length moderately narrow base. Color—near Pecan Brown, Plate XXVIII (Ridgway). Small prickles—none. Hairs—none.

*New shoots.*—Color—near Lettuce Green, Plate V (Ridgway). Large prickles—few; hooked slightly downward; with medium length moderately narrow base. Color—near Fluorite Green, Plate XXXII (Ridgway), shaded with near Corinthian Purple, Plate XXVIII (Ridgway). Small prickles—none. Hairs—none.

I claim:

A new and distinct variety of rose plant of the hybrid tea class, substantially as herein shown and described, characterized particularly as to novelty by having few to no prickles on its long flowering stems on which the blooms are usually borne singly, by the better than average lasting quality of its blooms, by the semi-double, initially high-centered form of the blooms, becoming saucer-shaped with maturity, by the orange-red general color tonality of the petals of its blooms, by the wider and longer than average size and the better than average substance of the petals, and by the prominent veins showing in the petals throughout the life of the blooms.

HERBERT C. SWIM.

No references cited.